United States Patent [19]

Artico et al.

[11] Patent Number: 5,278,184

[45] Date of Patent: Jan. 11, 1994

[54] SYNTHETIC DERIVATIVES OF PYRROLE AND PYRROLIDINE SUITABLE FOR THE THERAPY OF INFECTIONS CAUSED BY RHINOVIRUSES

[75] Inventors: Marino Artico, Rome; Federico Corelli, Siena; Silvio Massa; Antonello Mai, both of Rome; Enzo Tramontano, Nuoro, all of Italy

[73] Assignee: Repla Chemical Ltd., Vaduz, Liechtenstein

[21] Appl. No.: 870,625

[22] Filed: Apr. 17, 1992

[30] Foreign Application Priority Data

Apr. 19, 1991 [IT] Italy .................. MI 91 A 001096

[51] Int. Cl.$^5$ ............................................. A61K 31/40
[52] U.S. Cl. ...................................... 514/423; 514/247;
514/252; 514/256; 514/372; 514/374; 514/399;
514/406; 514/401; 544/335; 544/369; 544/379;
544/386; 544/399; 548/236; 548/336.1;
548/341.1; 548/333.5; 548/374.1; 548/375.1;
548/376.1; 548/517; 548/518; 548/562; 549/64;
549/499
[58] Field of Search ............... 514/423; 548/562, 571,
548/517, 518

[56] References Cited

U.S. PATENT DOCUMENTS

| 4,205,078 | 5/1980 | Satzinger | 548/518 |
|---|---|---|---|
| 4,857,539 | 8/1989 | Diana et al. | 514/378 |
| 4,861,791 | 8/1989 | Diana et al. | 548/237 |
| 5,071,844 | 12/1991 | Alker et al. | 548/517 |
| 5,100,893 | 3/1992 | Stokbroekx et al. | 544/237 |
| 5,118,682 | 6/1992 | Lubisch | 548/571 |
| 5,192,795 | 3/1993 | Zoller et al. | 514/423 |

FOREIGN PATENT DOCUMENTS 0137242 4/1985 .
0207453 1/1987 .

OTHER PUBLICATIONS

Massa et al. Bio org. Med. Chem. Lett. vol. 1 No. 11 pp. 575-578 (1991).
Massa et al. Chem. ABSTR. vol. 116 entry 120389 u (1991).
Journal of Medicinal Chemistry, vol. 28, No. 12, Dec. 1985, pp. 1906-1910, Washington, DC, US; G. D. Diana et al.

Primary Examiner—Donald G. Daus
Attorney, Agent, or Firm—Hedman, Gibson & Costigan

[57] ABSTRACT

Antirhinoviral compounds having the formula

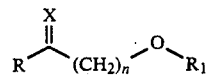

wherein R is hetrocyclic, particularly pyrrole or pyrrolidine, X is $H_2$ or O, n IS 3 to 7, and $R_1$ is substituted phenyl are disclosed.

4 Claims, No Drawings

SYNTHETIC DERIVATIVES OF PYRROLE AND PYRROLIDINE SUITABLE FOR THE THERAPY OF INFECTIONS CAUSED BY RHINOVIRUSES

PRIOR ART

From an antigenic point of view, human rhinoviruses (HRV) form an extremely heterogeneous group of picornaviruses, since they occur in over 100 different serotypes. This is one reason why they are a target that can be hardly hit by the traditional immunoprophylactic approach.

Therefore, the greatest hopes for the prophylaxis/therapy of infections caused in man by HRV are placed in antiviral chemotherapic drugs.

In the past ten years, several products, such as: 4',6-dichloroflavan (BW-683C) (Bauer, D. J.; Selway, J. W. T.; Batchelor, J. F.; Tisdale, M.; Cladwell, I. C.; Young, D. A. B.: Nature 1981, 292; 369–372), 4-ethoxy-2'-hydroxy-4',6-dimethoxychalcone (RO 09-0410) (Ninomiya, Y.; Ohsawa, C.; Aoyama, M.; Umeda, I.; Suhara, Y.; Tshitsuka, H.: Virology 1984, 134, 269–276), 1-[5-(tetradecyloxy)-2-furanyl]ethanone (RMI-15,731) (Ash, R. J.; Parker, R. A.; Hagan, A. C.; Mayer, G. D.: Antimicrob. Agents Chemother. 1979, 16, 301–305), and 5-{7-[4-(4,5-dihydro-2-oxazolyl)phenoxy]heptyl}-3-methyl-isoxazole (WIN 51711) (Diana, G. D.; McKinlay, M. A.; Otto, M. J.; Akullian, V.; Oglesby, R. C.: J. Med. Chem. 1985, 28, 1096–1910), were reported to inhibit a wide range of rhinoviruses by interaction with proteins of the virus capsid (Ninomya, G. D.; Aoyama, M.; Umeda, I.; Suhara, Y.; Tshitsuka, H.: Antimicrob. Agents Chemother. 1985, 27, 595–599) (Fox, M. P.; Otto, M. J.; McKinlay, M. A.: Antimicrob. Agents Chemother. 1986, 30, 110–116).

More detailed investigations on the structure/activity relationships were carried out on (oxazolinylphenyl)-isoxazoles. In fact, several structural analogs of WIN 51711 were synthesized, which differed not only in the length of the carbon atom bridge between the isoxazole and the phenyl rings, but also in the positions of the phenyl and/or oxazoline substituents (Diana, G. D.; Oglesby, R. C.; Akullian, V.; Carabateas, P. M.; Cutcliffe, D.; Mallamo, J. P.; Otto, M. J.; McKinlay, M. A.; Maliski, E. G.; Michalec, S. J.: J. Med. Chem. 1987, 30, 383–388) (Diana, G. D.; Cutcliffe, D.; Oglesby, R. C.; Otto, M. J.; Mallamo, J. P.; Akullian, V.; McKinlay, M. A.) (Diana, G. D. ; Treasurywala, A. M.; Bailey, T. R.; Oglesby, R. C.; Pevear, D. C.; Dutko, F. J.: J. Med. Chem. 1990, 33, 1306–1311).

In vitro, several compounds of this series were cytotoxic to uninfected cells in a range of concentrations between 3 and 30 $\mu$M and were active against HTV at different concentrations depending on the HRV serotype under examination.

Therefore, the need of finding new substances with a high activity against HRV and, at the same time, a low cytotoxicity was deeply felt.

SUMMARY

This invention relates to new synthetic compounds suitable for the therapy of infections caused by rhinoviruses having general formula (I)

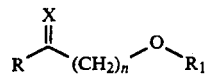

where:

R =
penta- or hexa-atomic heterocyclic radical, either saturated or non-saturated, which contains or does not contain substituents such as halogens, alkyls, or formyl,
cycloalkyl;

X = $H_2$, O, N—O—$R_2$, where $R_2$ = H, alkyl;

n = integer from 3 to 7;

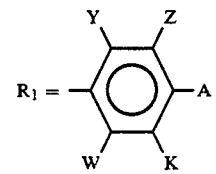

where Y, Z, W, K = H, halogen, $NO_2$, $CH_3$, $CF_3$, CHO, O-alkyl, —CH = $CH_2$;

A = $COOR_3$, where $R_3$ = H, alkyl;

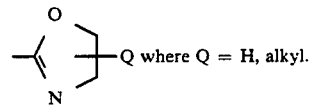

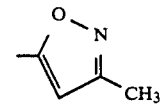

In the pharmacological assays said substances showed a high activity against rhinoviruses and a cytotoxicity to uninfected cells from 10 to 100 times lower than that of the compounds previously disclosed.

DETAILED DESCRIPTION OF THE INVENTION

The characteristics and advantages of the compounds disclosed in this invention, which are suitable for the therapy of infections caused by rhinoviruses, will be described in detail hereinafter.

Said compounds have general formula (I)

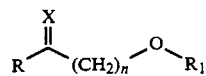

where:

R =
penta- or hexa-atomic heterocyclic radical, either saturated or non-saturated, which contains or does not contain substituents such as halogens, alkyls, or formyl,
cycloalkyl;

X = $H_2$, O, N—O—$R_2$, where $R_2$ = H, alkyl;

n = integer from 3 to 7;

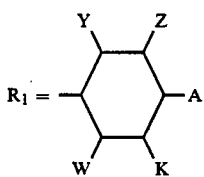

where Y, Z, W, K=H, halogen, NO₂, CH₃, CF₃, CHO, O-alkyl, —CH=CH₂;
A=COOR₃, where R₃=H, alkyl;

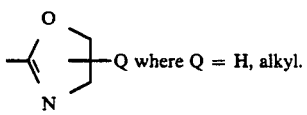

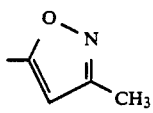

Preferred are the compounds in which R is a pyrrole, pyrrolidine, furan, thiophene, imidazole, pyrazole, piperazine, pyrimidine or cycloalkyl C₃-C₇ radical and the alkyl is an alkyl C₁-C₆ radical.

Even more preferred are the compounds having the following formulas:

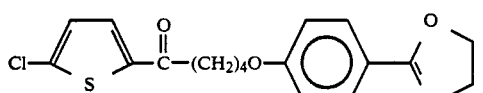 (366)

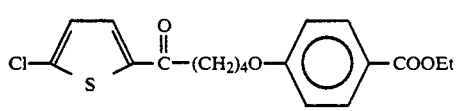 (360)

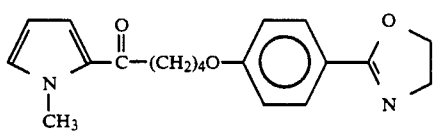 (414)

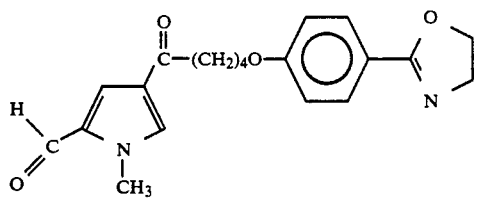 (395)

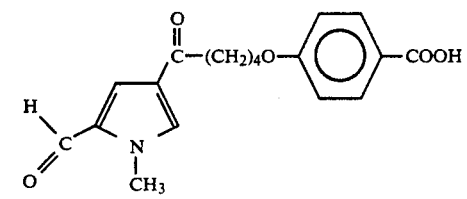 (394)

Compounds according to this invention can be prepared according to schemes I, II, III reported hereinafter.

Penta-atomic heterocyclic compounds such as pyrrole (2a), 1-methylpyrrole (2b), 2-chlorothiophene (2c), and 2-methylfuran (2d) were caused to undergo Friedel-Crafts acylation with 5-chlorovalerylchloride to obtain heteroarylketones (3a-d), which, by nucleophylic substitution with 4-(4,5-dihydro-2-oxazolyl)phenol, ethyl 4-hydroxybenzoate and N-(4-hydroxybenzoyl)ethanolamine in the presence of sodium iodide and K₂CO₃ gave compounds (4a-c), (5c,d), and (6), respectively.

Analogously, the reaction of ethyl 4-hydroxybenzoate and of 4-(4,5-dihydro-2-oxazolyl)phenol with a haloalkyl derivative (7), obtained by reduction of (3c) with LiAlH₄/AlCl₃, gave compounds (8) and (9), respectively. Finally, the hydrolysis of esters (5c) and (8) gave the corresponding carboxylic acids (10) and (11) (scheme I).

The synthesis of disoxaryl analogs with 3-pyrrolyl as heteroaromatic head was obtained as shown in scheme II.

1-Benzosulphonylpyrrole was acylated with 5-chlorovaleryl chloride to give intermediate (12), which by treatment with NaOH in a dioxane aqueous solution (50%) dropped the sulphonyl group and gave 3-(5-chlorovaleryl)pyrrole (13). The subsequent reaction with 4-(4,5-dihydro-2-oxazolyl)phenol gave compound (14). 1-Methylpyrrole (2b) was treated with Vilsmeier-Haak's reagent obtained from DMF and POCl₃ and with 5-chlorovalerylchloride/AlCl₃. Water treatment of the reaction mixture gave 4-(5-chlorovaleryl)-1-methylpyrrole-2-carboxyaldehyde (15), which was caused to react with 4-(4,5-dihydro-2-oxazolyl)phenol and ethyl-4-hydroxybenzoate to form derivatives (16) and (17), respectively. Alkaline hydrolysis of the latter gave carboxylic acid (18).

Alkylation of 4-(4,5-dihydro-2-oxazolyl)phenol with excess 1,5-dibromopentane (scheme III) gave intermediate (19), which by treatment either with pyrrole in the presence of NaH or with pyrrolidine gave compounds (20) and (21).

This invention particularly relates to a process for the preparation of compounds having general formula (I)

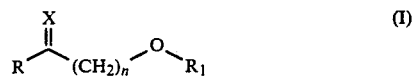 (I)

where R is

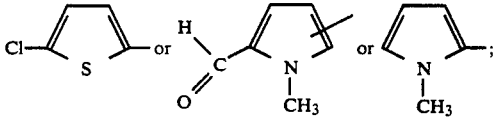

R₁ is

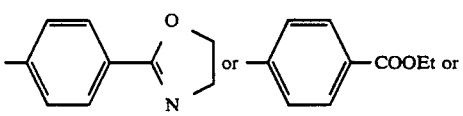

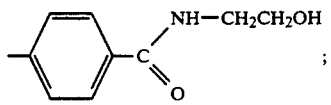

X=H₂ or O, and n = integer from 3 to 7
by reaction of compounds having formula
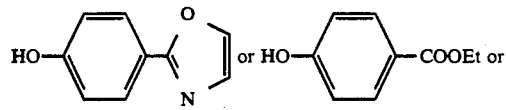
with compounds having formula
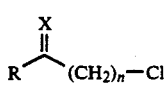
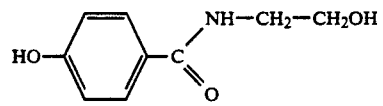
respectively,
in acetonitrile, in the presence of sodium iodide and anhydrous potassium carbonate under reflux conditions and in a molar ratio of the two reagents between 1:1.2 and 1:0.8.
SCHEME I
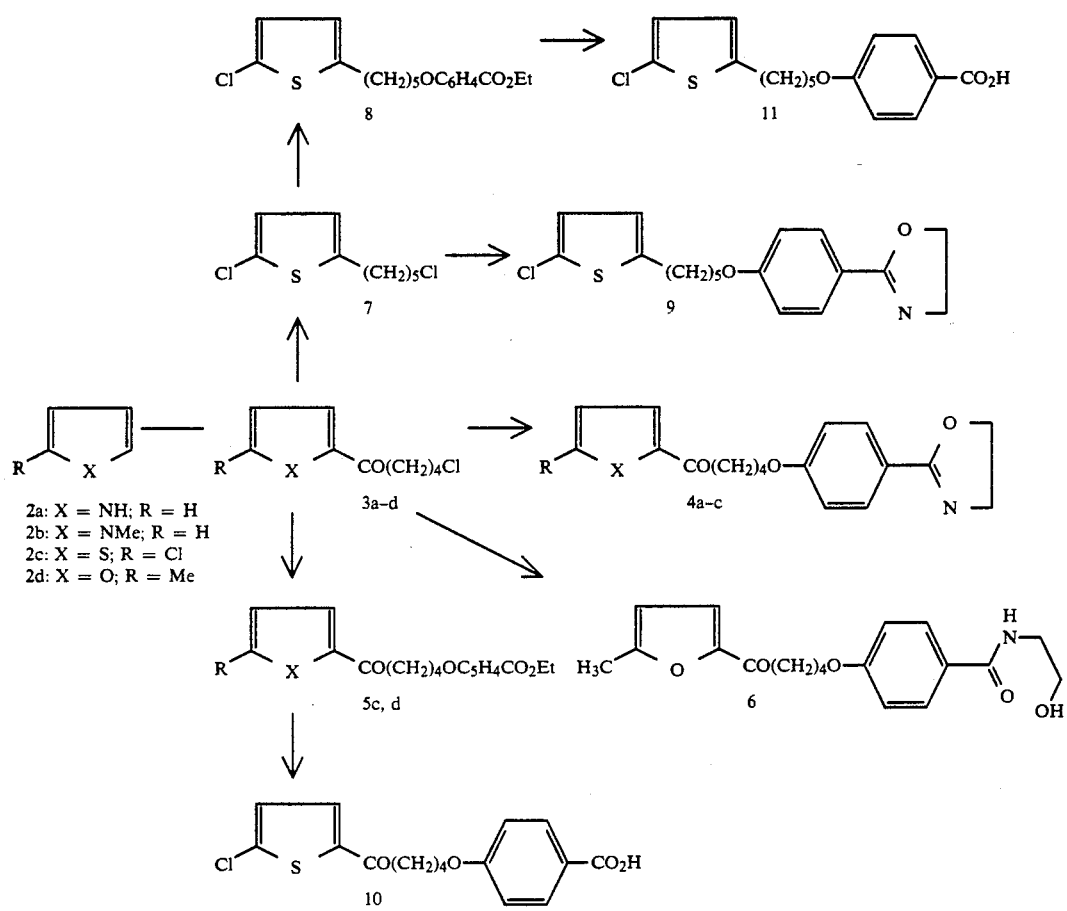
SCHEME II
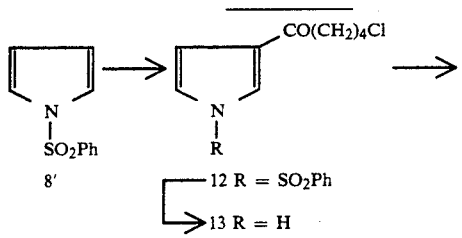

-continued
SCHEME II

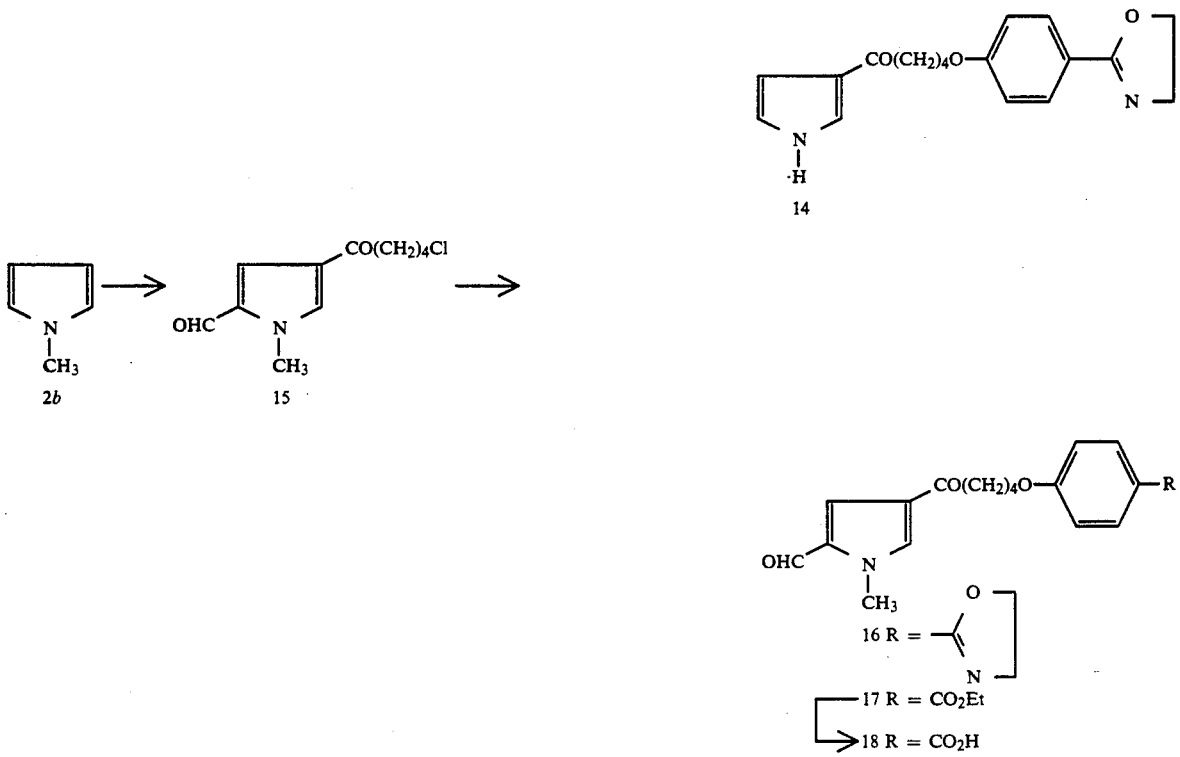

SCHEME III

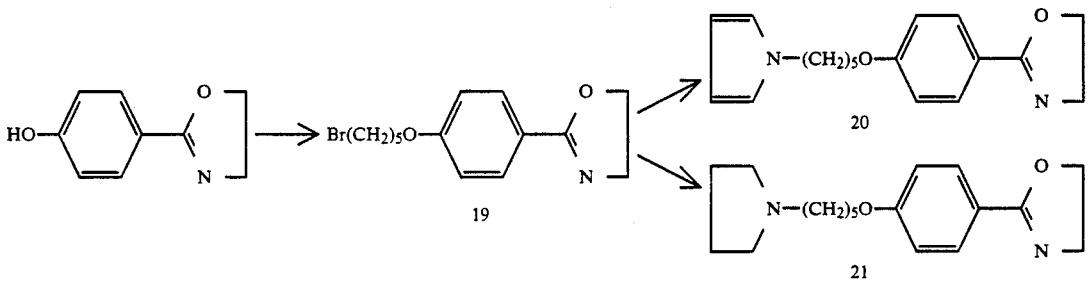

Said compounds, mixed with pharmacologically acceptable diluents and excipients, can be used to prepare pharmaceutical compositions suitable for the therapy of infections caused by rhinoviruses.

It follows that said compositions consist of pharmacologically active quantities of said compounds and of pharmacologically acceptable diluents and excipients.

The following examples illustrate the process for the preparation of compounds 4c, 5c, 9, and 18. These examples are illustrative only; in no event are they to be regarded as limiting the scope of the claimed invention.

EXAMPLE 1

2-Chloro-5-{5-[4-(4,5-dihydro-2-oxazolyl)phenoxy]pentanoyl}thiophene (4c)

A solution of 5-chloropentanoyl chloride (7.75 g, 0.05 mol) and aluminium trichloride (6.67 g, 0.05 mol) in the same solvent (60 ml) was slowly added to a solution of 2-chlorothiophene (5.93 g, 0.05 mol) in 1,2-dichloroethane (60 ml). The resulting solution was stirred for 20 min. at room temperature, refluxed for 1 hr., cooled and poured on ice (300 ml) containing conc. hydrochloric acid (30 ml). The organic phase was separated, washed with water, and dried on anhydrous sodium sulfate. By solvent removal at a reduced pressure a homogeneous oil (TLC: silicon dioxide-benzene) was obtained, which slowly solidified to pure 3c (11.26 g; 95%). M.p. 37°-38° C. (via ethyl ether). Anal. ($C_9H_{10}Cl_2OS$).

A mixture consisting of 2-chloro-5-(5-chloropentanoyl)thiophene (3c) (2.13 g, 0.009 mol), sodium iodide (1.1 g, 0.0073 mol), 2-(4-hydroxyphenyl)-4,5-dihydrooxazole (1.99 g, 0.010 mol), and anhydrous potassium carbonate (5.2 g, 0.045 mol) in acetonitrile (50 ml) was refluxed for 48 hrs., cooled and filtered. The resulting solution was deprived of the solvent and the residue was taken up with ethyl acetate (100 ml). After washing with water and subsequent drying on anydrous sodium sulfate the solution was evaporated to dryness. The resulting solid was crystallized via benzene:cyclohexane (1:1) to give pure 4c (3.17 g; 97%). M.p. 143°-144° C. Anal. ($C_{18}H_{18}ClNO_3S$).

EXAMPLE 2

2-Chloro-5{5-[4-(ethoxycarbonyl)phenoxy]pentanoyl}thiophene (5c)

A mixture consisting of 2-chloro-5-(5-chloropentanoyl)thiophene (3c) (2.13 g, 0.009 mol), sodium iodide (1.1 g, 0.0073 mol), 4-hydroxyethylbenzoate (1.7 g, 0.010 mol), and anhydrous potassium carbonate (6.2 g, 0.045 mol) in acetonitrile (50 ml) was refluxed for 24 hrs., cooled, and filtered. The resulting solution was deprived of the solvent and the residue was taken up with dichloromethane (100 ml). After washing with water and subsequent drying on anydrous sodium sulfate the solution was evaporated to dryness. The resulting solid was crystallized via cyclohexane to pure 5c (2.5 g; 76%). M.p. 87°-89° C. Anal. ($C_{18}H_{19}ClO_4S$).

EXAMPLE 3

2-Chloro-5-{5-[4-(4,5-dihydro-2-oxazolyl)phenoxy]pentyl}thiophene (9).

A solution of 2-chloro-5-(5-chloropentanoyl)thiophene (3c) (1.18 g, 0.005 mol) and aluminum trichloride (0.66 g, 0.005 mol) in anhydrous ethyl ether (40 ml) and tetrahydrofuran (30 ml) was slowly added to a mixture, cooled to 0°-5° C., consisting of lithium and aluminium hydride (1.33 g, 0.01 mol) in anhydrous ethyl ether (40 ml). The reaction mixture was magnetically stirred for 6 hrs. at 30°-40° C., cooled to 0°-5° C., and cautiously diluted with water (20 ml) and 6N hydrogen sulphate (20 ml). The organic phase was separated, washed with water, and dried on anhydrous sodium sulphate. Solvent removal gave a chromatographically pure liquid residue (TCL: silicon dioxide-cyclohexane) consisting of 7 (0.99 g; 89%), which was directly used in the subsequent reaction with 2-(4-hydroxyphenyl)-4,5-dihydrooxazole, as described for the preparation of 4c, to give 9 (0.81 g; 52%) (after crystallization via cycloexane). M.p. 99°-100° C. Anal. ($C_{18}H_{20}ClNO_2S$).

EXAMPLE 4

4-{5-[4-(Carboxy)phenoxy]pentanoyl}-2-formyl-1-methyl-1H-pyrrole (18).

A solution of oxalyl chloride (1.27 g, 0.01 mol) in the same solvent (20 ml) was added over 5-10 min. to a solution of N,N-dimethylformamide (0.78 ml, 0.01 mol) in 1,2-dichloroethane (20 ml). The reaction mixture was stirred for 15 min. at room temperature, cooled to 0°-5° C., and rapidly added with a solution of 1-methylpyrrole (0.89 ml, 0.01 mol) in 1,2-dichloroethane (20 ml). The resulting mixture was stirred for 15 min. at room temperature and added in a rapid sequence with aluminium trichloride (2.92 g, 0.022 mol) and 5-chloropentanoyl chloride (1.3 ml, 0.01 mol). Two and a half hours later the mixture was poured on ice (100 ml) containing sodium hydroxide (50%; 10 ml). Fifteen minutes later the mixture was acidified with hydrochloric acid (37%). The organic phase was separated and the aqueous phase was extracted with chloroform (2×50 ml). The organic extracts collected were washed with water, dried on anhydrous sodium sulphate, and evaporated at a reduced pressure. The product obtained was a dark oil, which solidified slowly and was purified chromatographically in silica gel column, using chloroform as an eluent. Pure 15 (1.75 g; 77%) was thus obtained. M.p. 43°-46° C. Anal. ($C_{11}H_{14}ClNO_2$).

4-{5-[4-(Ethoxycarbonyl)phenoxy]pentanoyl}-2-formyl-1-methyl-1H-pyrrole (17) was obtained from compound 15 (yield: 76%) by the operating procedure described for the preparation of 5c. Compound 17 was a clear solid which, after crystallization via ethanol, had m.p. of 117°-118° C. Anal. ($C_{20}H_{23}NO_5$).

A mixture consisting of 17 (3.56 g, 0.01 mol), 2N potassium hydroxide and ethanol (95%; 35 ml) was stirred for 5 hrs. at 70° C. The resulting solution was diluted with water (70 ml), acidified with 12N hydrochloric acid, and extracted with ethyl acetate (3×20 ml). The collected organic extracts were washed with a saturated solution of sodium chloride to neutralization, dried on anhydrous sodium sulphate, and deprived of the solvent. A yellowish solid consisting of compound 18 was obtained (2.26 g; 69%). The product was found to be pure by thin-layer analysis (silicon dioxide-ethyl acetate:acetic acid 50:1). M.p. 181°-183° C. (via toluene). Anal. ($C_{18}H_{19}NO_5$).

PHARMACOLOGICAL ASSAYS

The assays concerned the cytotoxicity and antiviral activity of compounds having general formula (I).

The activity against Herpes Simplex Virus type 1 (HSV-1), Virus Vaccinicum (VV), Vesicular Stomatitis Virus (VSV), Coxsackie Virus B1 (Coxs) and Poliomyelitis Virus type 1 (Sb-1) was determined on Vero cells monolayers at 37° C.

HRV-14 was used as a representative of the HRV, its degree of sensitivity toward the compounds disclosed in the past being most predictive of the sensitivity of a wider range of different serotypes (Diana, G. D.; Oglesby, R. O.; Akullian, V.; Carabateas, P. M.; Cutliffe, D.; Mallamo, J. P.; Otto, M. J.; McKinlay, M. A.; Maliski, E. G.; Michalec, S. J.: J. Med. Chem. 1987, 30, 383–388; Diana, C. D.; Cutliffe, D.; Oglesby, R. O.; Otto, M. J.; Mallamo, J. P.; Akullian, V.; McKinlay, M. A.: J. Med. Chem. 1989, 32, 450–455).

The antiviral activity assay was carried out on HeLa cells monolayers at 33° C.

All the compounds used in this investigation were dissolved in dimethyl sulfoxide at concentrations 200 times higher than the maximum dose used. The resulting stock solutions were diluted in MEM to obtain final concentrations varying between 200 µg/ml and 0.005 µg/ml.

Assays on the reduction in the number of viral plaques

The culture medium was sucked from confluent monolayers of Vero and HeLa cells (Ohio). Said monolayers were infected by different viruses diluted as required (0.2 ml/trough) to inoculate ca. 150 plaque/trough-forming units. The cultures were incubated for 1 hr. at 37° C. (33° C. in the case of HRV-14), which temperature was controlled by a thermostat (5% $CO_2$) (2% in the case of HRV-14). The inocula were removed and the cell monolayers were added with MEM containing calf serum (2%), carboxymethylcellulose (0.75%), and compounds to be assayed at the concentrations reported above. The culture medium for HRV-14 contained also $MgCl_2$ (30 mM) and DEAE-dextran (15 µg/ml).

The controls, i.e. the monolayers that had been infected but not treated and the monolayers that had been treated but not infected (for the determination of the cytotoxicity of the compounds) were included in the same assay.

All cultures were incubated for 3-4 days at 37° C. (33° C. in the case of HRV-14), which temperature was controlled by a thermostat (5% CO2) (2% in the case of HRV-14). Monolayers were fixed with 5% formaldehyde in a 2% sodium acetate solution and dyed in the fixing solution with 0.25% crystal violet. The plaques, i.e. the clear areas produced by the virus destructive action on the cells, could thus be counted. The compound concentration, which was obtained from a 50% reduction in the number of plaques, was determined for each virus by linear regression and reported as minimal inhibitory concentration (MIC).

Cytotoxicity assays

The maximum concentration of assayable compound (MTL) was the highest concentration producing no cytotoxic effect.

RESULTS

The results obtained from cytotoxicity and antiviral activity assays are shown in Table 1. The same table reports, for comparison, also the data obtained using two out of the compounds previously known, which were found to be more active on a wide HRV range.

In HeLa cells, like in uninfected Vero cells, the compounds disclosed in this invention show much higher MTL values than those obtained with the previously known compounds, i.e. the compounds as per this invention are less toxic.

As concerns the antiviral activity, all assayed compounds can inhibit HRV-14 only.

Against said virus, the most effective compound (0.05 $\mu$M) is 366, followed by 414, and by 360. The three compounds have low cytotoxicity levels and, therefore, selectivity indices (MTL/MIC ratio) higher than 8200, 762, and 272, respectively.

Compared with the two previously known compounds, 395 and 394 are less effective, but even more selective to HRV-14.

The invention refers therefore also to the use of the compounds of general formula (I) in the therapy of infections caused by rhinoviruses. The therapeutical method consists in administering effective quantities of said compounds by oral or parenteral route. Intranasal administration: from 50 to 2000 ug, preferably from 100 to 1000 ug, 3–6 times a day, alone or with excipients (cyclodextrins, liposomes) which may accelerate the absorption, or of lipo-water-soluble nature.

Oral administration: from 0.1 to 50 mg/Kg, preferably 0.5 to 30 mg/Kg, 1–3 times a day, alone or with gastro-resistant excipients.

The anti-HRV-14 cytotoxicity and activity assays were also carried out on other four compounds of the present invention, i.e. on 529 (2-[5-[4-(4,5-Dihydro-2-oxazolyl)phenoxy]pentanoyl]-4-methylthiophene), 522 2-[5-[4,5-Dihydro-2-oxazolyl)phenoxy]pentanoyl]-5-methylthiophene), 514 (2-[5-[4-ethoxycarbonyl)phenoxy]pentanoyl]-5-methylthiophen), 393 (4-[5-[4-(ethoxycarbonyl)phenoxy]pentanoyl]-1-methyl-1H-pyrrole-, -2-carboxaldeide).

The results are reported in Table 2.

Also these compounds, although less active than the WIN 51711 reference compound, resulted as much as or more selective as regards to HRV-14.

Results for the evaluation of the activity of 529, 522, 514 and 393 on a larger number of rhinoviruses serotypes are reported in Table 3.

360 (see Table 1) and the WIN 51711, as reference compound, were included in the same assay.

This assay was carried out following a different method from the one used in the assay illustrated in Tables 1 and 2. Said method, which was described in detail by Pauwels, R., Balzarini, J., Baba, M., Snoeck, R., Schols, D., Herdwijn, P. Desmyter, J. & De Clercq, E. (1988) J. Virol. Method 20, 309–321, is reported in brief hereinafter.

Monolayers of HeLa cells (Ohio) ($3.5 \times 10^4$ cells/well) were treated with scalar dilutions of the compounds under examination in MEM containing 2% calf serum, Mg $Cl_2$, 30 mM and DEAE-dextran, 15 $\mu$g/ml. Cultures were then infected by appropriate dilutions of different rhinoviruses serotypes, so that, within 72 hours the total destruction of monolayer in the infected but not treated cultures, was obtained. (Inoculum variable from 500 and 1000 plaque-forming units).

The controls represented by not infected but treated monolayers (for the determination of the cytotoxicity of the compounds) were part of the same assay.

The cultures were incubated for 72 h at 33° C. The number of vital cells in infected but not treated controls, in treated but not infected controls and in the cultures, infected and treated at different dilutions of the compounds under examination, was determined by adding MTT [3-4,5-dimethylthiazol-2-yl)-2,5-diphenyltetrazoliumbromide]. The doses of every compound, necessary to protect against death caused by infection propagation 50% of the cells, were then counted.

At the concentration levels used in the present assay, no compound was found cytotoxic.

TABLE 1

| COMPOUND | (a)MTL ($\mu$M) Vero | (b)MIC MSV-1 | VV | VSV | Coxs | Sb-1 | MTL ($\mu$M) HeLa | MIC HRV-14 | (c)S.I. |
|---|---|---|---|---|---|---|---|---|---|
| 366 | >275 | >275 | >275 | >275 | >275 | 200 | >410 | 0.05 | >8200 |
| 360 | >190 | >190 | >190 | >190 | >190 | 80 | >545 | 2.0 | >272 |
| 414 | >300 | >300 | >300 | >300 | >300 | >300 | >610 | 0.8 | >762 |
| 395 | >280 | >280 | >280 | >280 | >280 | >280 | >425 | 5.0 | >85 |
| 394 | 380 | >380 | >380 | >380 | >380 | >380 | >610 | 7.0 | >87 |
| 1 (WIN 51711) (comparison) | | | | | | | $^d$18 | $^e$0.4 | 45 |
| 15 (comparison) | | | | | | | $^f$16 | $^f$1.2 | 13 |

(a) MTL (max. non-toxic dose): highest compound that causes no apparent effects on the cell monolayers.
(b) MIC (50% effective dose): compound concentration needed for 50% plaques reduction. The plaques number in untreated control cultures was: 150 (HSV-1), 120 (VV), 154 (VSV), 160 (Coxs), 115 (Sb-1), 130 (HRV-14).
(c) S.I. (Selectivity Index): MTL/MIC ratio.
$^d$Value for compound 1 from Table II in "Diana G.D., Oglesby R.C., Akullian V., Carabateas P.M., Cutcliffe D., Mallamo J.P., Otto M.J., McKinlay M.A., Maliski E.G. and Michalec S.J.. J. Med. Chem. 30, 383–388 (1987)".
$^e$Value for WIN 51711 from Table 7 in "Smith T.J., Kremer M.J., Luo M., Vriend G., Arnold E., Kamer G., Rossmann M.G., McKinlay M.A., Diana G.D., Otto M.J.. Science 233, 1286–1293 (1986)".
$^f$Value for compound 15 from Tables I and II in "Diana G.D., Cutcliffe D., Oglesby R.C., Otto M.J., Mallamo J.P., Akullian V. and McKinlay M.A.. J. Med. CHem. 32, 450–455 (1989)".

The compounds of the present invention resulted more effective and/or more selective than the reference compound WIN 51711 also as rhinoviruses inhibiting agent having a wide range spectrum.

In particular, 514 and 360 resulted the most effective and selective.

TABLE 2

| COMPOUND | $^a$MTL HeLa | (μM) | $^b$MIC HRV-14 | $^c$S.I. |
|---|---|---|---|---|
| 529 | 291 | | 6.9 | 42 |
| 522 | >291 | | 2.9 | >100 |
| 514 | >578 | | 3.4 | >170 |
| 393 | 50 | | 1.4 | 36 |
| 1 (WIN 51711) | $^d$18 | | $^e$0.4 | 45 |

$^a$MTL (maximum testable level): highest concentration of compound that causes no apparent effects on the cell monolayers.
$^b$MIC (Minimum Inhibitory Concentration): drug dose required to reduce the number of HRV-14 plaques by 50%. The plaque number in untreated cultures was 105.
$^c$S.I. (Selectivity Index): ratio MTL/MIC.
$^d$Value for compound 1 (WIN 51711) from Table II in "Diana G.D., Oglesby R.C., Akullian V., Carabateas P.M., Cutcliffe D., Mallamo J.P., Otto M.J., McKinlay M.A., Malliski E.G. and Michalec S.J., J. Med. Chem. 30, 383-388 (1987)".
$^e$Value for WIN 51711 from Table 7 in "Smith T.J., Kremer M.J., Luo M., Vriend G., Arnold E., Kamer G., Rossmann M.F., McKinlay M.A., Diana G.D., Otto M.J.. Science 1286-1293 (1986)".

TABLE 3

| COMPOUND | $^a$MIC (μM) | | | | | | | | | $^b$MIC | $^c$S.I. |
| | 2 | 14 | 15 | 21 | 22 | 30 | 50 | 86 | 89 | | |
|---|---|---|---|---|---|---|---|---|---|---|---|
| 529 | 2.9 | 1.1 | 0.2 | 5.8 | 11.6 | 5.8 | 4.3 | 0.9 | 2.9 | 4.1 | 71 |
| 522 | 1.1 | 0.3 | 0.3 | 1.7 | 11.6 | 1.4 | 1.1 | 0.14 | 0.3 | 2.0 | >145 |
| 514 | 0.5 | 1.7 | 0.9 | 0.1 | 1.4 | 0.14 | 0.4 | 0.14 | 0.3 | 0.63 | >917 |
| 393 | 0.5 | 2.0 | 2.2 | 2.2 | 1.1 | 1.1 | 0.8 | 0.14 | 0.2 | 1.4 | 36 |
| 360 | 0.1 | 2.7 | 1.6 | 0.0 | 1.4 | 0.05 | 0.4 | 0.3 | 0.3 | 0.76 | >717 |
| WIN 51711 | 1.7 | 0.6 | 0.3 | 0.6 | 3.5 | 1.7 | 2.0 | 0.06 | 0.9 | 1.2 | 23 |

$^a$MIC: drug dose required to protect by 50% HeLa cells from rhinovirus-induced cytopathogenicity.
$^b$MIC: mean MIC for nine serotypes
$^c$S.I.: ratio MTL (see Table 1 or 2)/MIC.

We claim:

1. Derivatives having the formula:

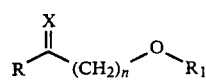

(1)

wherein: R is a heterocyclic radical selected from the group consisting of pyrrole and pyrrolidine radicals having one or two substituents selected from the group consisting of halogens, alkyls of 1-6 carbon atoms and formyl;

X is selected from $H_2$, O and $N-O-R_2$ wherein $R_2$ is H or alkyl of 1-6 carbon atoms;
n is an integer of from 3 to 7;

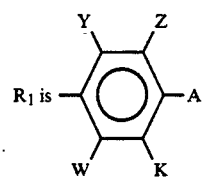

$R_1$ is wherein Y, Z, W, and K are selected from the group consisting of H, halogen, $NO_2$, $CH_3$, $CF_3$, CHO, O-alkyl of 1 to 6 carbon atoms, and $-CH=CH_2$;

A is $COOR_3$, wherein $R_3$ is selected from H and alkyl of 1 to 6 carbon atoms.

2. Derivatives as defined in claim 1 which have the formula:

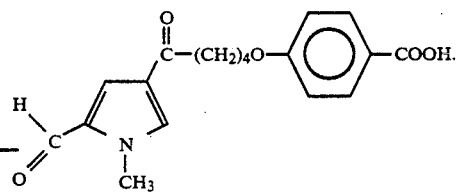

3. A pharmaceutical composition for the therapy of rhinovirus infections, said composition consisting essentially of a pharmacologically effective amount of a compound of claim 1 and pharmacologically acceptable diluents and excipients.

4. A method for the treatment of infections caused by rhinoviruses, said method comprising the oral or parenteral administration of an effective amount of a compound of claim 1.

* * * * *